United States Patent [19]

Agouridas et al.

[11] Patent Number: 5,614,614
[45] Date of Patent: *Mar. 25, 1997

[54] ERYHROMYCIN DERIVATIVES

[75] Inventors: Constantin Agouridas, Nogent Sur Marne; Alain Bonnefoy, Les Lilas; Jean-Francois Chantot, Gressy En France; Alexis Denis; Odile Le Martret, both of Paris, all of France

[73] Assignee: Roussel Uclaf, France

[*] Notice: The term of this patent shall not extend beyond the expiration date of Pat. No. 5,444,051.

[21] Appl. No.: 391,959

[22] Filed: Feb. 21, 1995

Related U.S. Application Data

[62] Division of Ser. No. 146,697, Nov. 1, 1993.

[30] Foreign Application Priority Data

Nov. 5, 1992 [FR] France .................................. 92 13320
Jul. 2, 1993 [FR] France .................................. 93 08109

[51] Int. Cl.$^6$ .................................................. C07H 17/08
[52] U.S. Cl. ............................................ 536/7.5; 536/7.2
[58] Field of Search ...................... 536/7.2, 7.5; 514/29

[56] References Cited

U.S. PATENT DOCUMENTS 5,444,051  8/1995  Agouridas et al. ....................... 514/29

*Primary Examiner*—Elli Peselev
*Attorney, Agent, or Firm*—Bierman & Muserlian

[57] ABSTRACT

Novel intermediates for the preparation of the compounds of Formula I wherein the substituents are as defined in the specification.

2 Claims, No Drawings

ERYHROMYCIN DERIVATIVES

PRIOR APPLICATION

This application is a continuation of U.S. Patent application Ser. No. 146,697 filed Nov. 1, 1993.

OBJECTS OF THE INVENTION

It is an object of the invention to provide the novel compounds of formula I and their non-toxic, pharmaceutically acceptable acid addition salts and a process for their preparation.

It is another object of the invention to provide novel antibiotic compositions and a novel method of combatting bacterial infections in warm-blooded animals.

These and other objects and advantages of the invention will become obvious from the following detailed description.

THE INVENTION

The novel compounds of the invention are selected from the group consisting of a compound of the formula

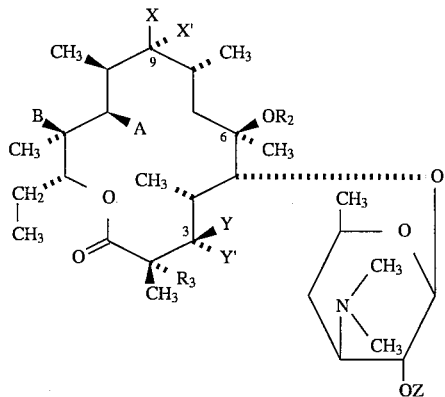

I wherein R is $-(CH_2)_n-Ar_1$ or $-XAr_2$, n is an integer from 1 to 6, $Ar^1$ and $Ar_2$ are individually selected from the group consisting of a) carbocyclic aryl of up to 18 carbon atoms substituted by at least one member of the group consisting of free carboxy, alkoxy carbonyl and carboxyl salified with a pharmaceutically acceptable base, —OH, halogen,

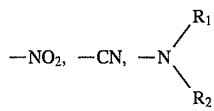

and alkyl, cycloalkyl, alkenyl, alkynyl, alkoxy, alkenyloxy, alkynyloxy, alkylthio, alkenylthio, alkynylthio, N-alkyl, N-alkenyl and N-alkynyl of up to 12 carbon atoms optionally substituted with at least one halogen, $R_1$ and $R_2$ are individually hydrogen or alkyl of 1 to 12 carbon atoms, b)

wherein $R_3$ is selected from the group consisting of alkyl of 1 to 12 carbon atoms, optionally substituted carbocyclic aryl, aryloxy and arylthio, optionally substituted heterocyclic aryl, aryloxy and arylthio containing at least one heteroatom with the optional substituents being those of carbocyclic aryl above, X is an alkyl of 1 to 6 carbon atoms interrupted by a member of the group consisting of —O—, —S—, —SO—, —SO$_2$, —CO—, —NH—C— and —C—NH—, Z is hydrogen or acyl of an organic carboxylic acid of up to 18 carbon atoms and their non-toxic, pharmaceutically acceptable acid addition salts.

Examples of suitable acids for the preparation of non-toxic, pharmaceutically acceptable acid addition salts are inorganic acids such as hydrochloric acid, hydrobromic acid, hydroidic acid, sulfuric acid and phosphoric acid and organic acids such as acetic acid, propionic acid, trifluoroacetic acid, maleic acid, tartaric acid, stearic acid, ethylsuccinic acid, methane sulfonic acid, benzenesulfonic acid, p-toluenesulfonic acid and laurylsulfuric acid.

Examples of carbocyclic aryl are phenyl and naphthyl and examples of monocyclic heteroaryl of 5 ring members are thienyl, furyl, pyrrolyl, thiazolyl, oxazolyl, imidazolyl, thiadiazolyl, pyrazolyl and isoxazolyl. Examples of monocyclic heteroaryl of 6 ring members are pyridyl, pyrimidinyl, pyridazinyl and pyrazinyl. Examples of condensed polycyclic heteroaryl are indolyl, benzofuryl, benzothienyl or quinolinyl or a purine base remainder such as adenine.

Examples of alkyl, alkenyl and alkynyl are methyl, ethyl, propyl, isopropyl, n-butyl, isobutyl, terbutyl, decyl or dodecyl, vinyl, allyl, ethynyl, propynyl and propargyl and examples of cycloalkyl are cyclobutyl, cyclopentyl and cyclohexyl. Halogen is preferably fluorine, chlorine or bromine and haloalkyl may be —CH—Cl$_2$, —CHBr$_2$, —CHF$_2$, —CCl$_3$, —CBr$_3$, —CF$_3$, —CH$_2$—CF$_3$, —CH$_2$—CH$_2$—CCl$_3$, —CH$_2$—CH$_2$—CF$_3$. Examples of acyl of an organic carboxylic acid are acetyl, propionyl, butyryl, isobutyryl, n-valeryl, isovaleryl, tert-valeryl and pivalyl.

Among the preferred compounds of formula I are those wherein Z is hydrogen, those wherein R is —(CH$_2$)$_4$—Ar$_1$ wherein Ar$_1$ has the above definition, those wherein Ar$_1$ is phenyl substituted with at least one halogen, preferably chlorine and most preferably 4-chlorophenyl or Ar$_1$ is phenyl substituted by at least one alkoxy of 1 to 4 carbon atoms, preferably methoxy and most preferably 4-methoxyphenyl and those wherein Ar$_1$ is optionally substituted heterocyclic aryl of 5 ring members, preferably optionally substituted thienyl and most preferably thienyl or an optionally substituted imidazolyl and most preferably imidazolyl.

Other preferred compounds of formula I are those wherein Ar$_1$ is an optionally substituted biphenyl of the formula

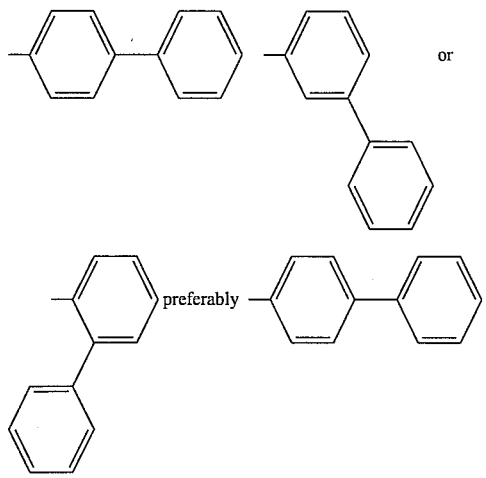

and those wherein R is —X$_1$Ar$_2$ wherein X$_1$ is alkyl of 1 to 6 carbons atoms interrupted by

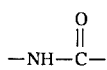

and Ar$_2$ is defined as above and preferably

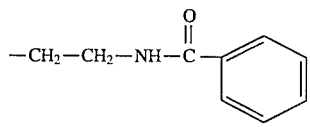

with phenyl being optionally substituted as indicated above.

The more preferred compounds of formula I are those of Examples 1, 2, 3, 4, 11 and 15 and especially the compounds of Examples 28, 38 and 39.

The novel process of the invention for the preparation of a compound of formula I comprises reacting a compound of the formula

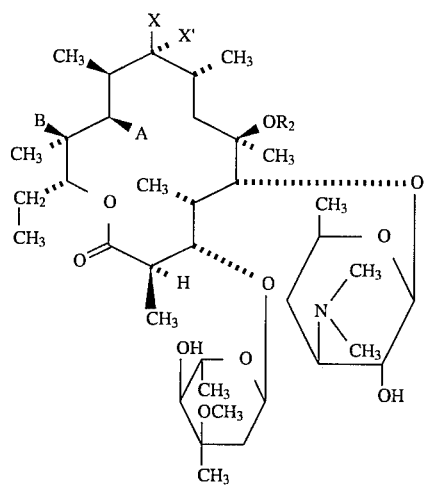

wherein Z' is acyl of an organic carboxylic acid of 1 to 18 carbon atoms with an agent capable of selectively activating the 11-hydroxyl to obtain a compound of the formula

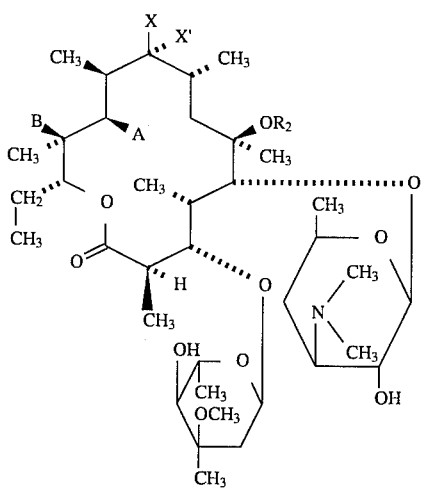

wherein R$_1$ is an easily cleavable group, subjecting the latter to the action of a base to obtain a compound of the formula

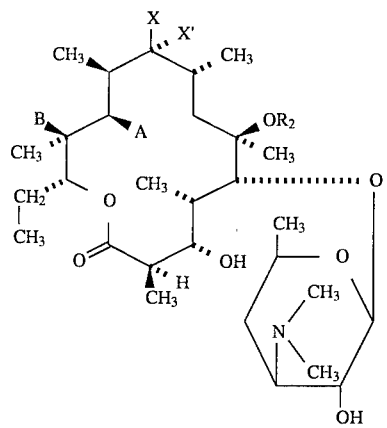

and either reacting the latter with a compound of the formula $$R-N=C=O \qquad V$$

wherein R has the above definitions to obtain a compound of the formula

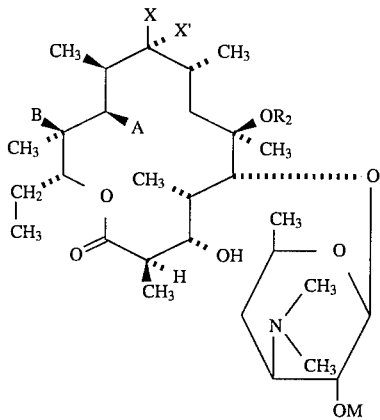

and cyclizing the latter spontaneously by heating or reaction with a cyclizing agent to obtain a compound of the formula

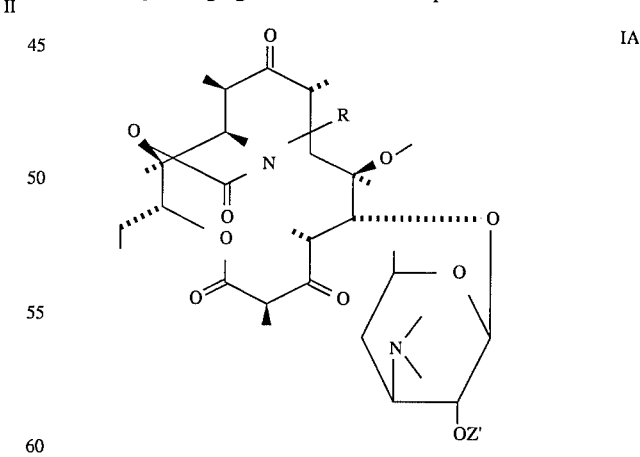

wherein Z' is other than hydrogen or by reacting a compound of formula IV with carbonyldiimidazole to obtain a compound of the formula

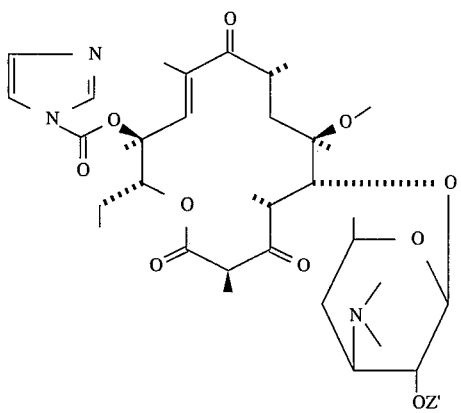

reacting the latter with a compound of the formula

RNH₂    VIII wherein R has the above definition to form a compound of formula VI and cyclizing the latter spontaneously by heating or by reaction with a cyclizing agent to obtain the compound of formula IA and optionally subjecting the latter to an agent capable of releasing the 2 hydroxy and optionally reacting the latter with an acid to form the acid addition salt.

In a preferred embodiment of the process, the agent capable of selectively activating the 11-hydroxy is a sulfonic acid anhydride such as methane sulfonic anhydride, p-toluene sulfonic anhydride or trifluoromethane sulfonic anhydride and the base to react with the compound of formula III to create 10(11) double bond is a diazabicyclonodecene such as DBU (1,8-diazabicyclo-[5-4-0]-undec-7-ene), diazabicyclononene, 2,6-lutidine, 2,4,6-collidine or tetramethylguanidine. The reaction between the compounds of formulae IV or V is effected in the presence of a base such as pyridine, triethylamine, morpholine or N-methyl-morpholine and the cyclization of the compound of formula VI is effected spontaneously or by heating at 50° to 100° C.

The reaction of a compound of formula IV with a carbonyldiimidazole is effected in the presence of a base such as sodium hydride, triethylamine or sodium or potassium carbonate or bicarbonate or in the absence of a base in an organic solvent such as tetrahydrofuran, methylene chloride or dimethylformamide. The reaction of a compound of formula VII with RNH₂ is effected in a solvent such as acetonitrile, dimethylformamide, tetrahydrofuran, dimethoxyethane or dimethylsulfoxide and the cyclization of the compound of the formula VI is effected during the reaction or achieved with a base such as potassium tert.-butylate on the isolated product in a solvent such as tetrahydrofuran. The hydrolysis of the 2'-ester is effected with methanol or aqueous hydrochloric acid and the salification may be effected with a stoichiometric amount of the desired acid.

The compounds of formula II are known and can be prepared by the process of European patent application No. 0,487,411 and the compounds of the formula RN=C=O and RNH₂ are known and can be prepared by the process described in J. Med. Chem. (1982), Vol. 25, p. 947, Tetrahedron Letters, Vol. 32, No. 14, pp. 1699–1702, (1991); J. Org. Chem., Vol. 54(18), pp. 4298–4301 (1989); J. Org. Chem., Vol. 28 (101), pp. 2589–2591 (1963), German Patent 3,406,416; J. Org. Chem., Vol. 6, pp. 895–901 (1941) or Synth. Commun., Vol. 17(14), pp. 1741–1748 (1987).

Certain products of formula VII are novel and their preparation is described infra. They include 4-(2,thienyl)-butylamine, 4-(1,1'-biphenyl)-butylamine, 4-(4-methylphenyl)-butylamine, 4-(2,4-dimethylphenyl)-butylamine, 4-(2,4,6-trimethyl-phenyl)-butylamine and 4-(2-methoxyphenyl)-butylamine. Also novel are the compounds of formulae III, IV and the corresponding 2'-OH compounds, VI and VII.

The novel antibiotic compositions of the invention are comprised of an antibiotically effective amount of a compound of formula I or its non-toxic, pharmaceutically acceptable acid addition salts and an inert pharmaceutical carrier. The compositions may be in the form of tablets, dragees, capsules, granules, gels, creams, ointments, suppositories or injectable solutions or suspensions or in powder for extemporaneous dissolution in an appropriate vehicle such as apyrogenic sterile water.

Examples of pharmaceutical carriers are talc, gum arabic, lactose, starch, magnesium stearate, cocoa butter, aqueous or nonaqueous vehicles, fatty substances of animal or vegetable origin, paraffins, glycols, various wetting agents, dispersants and emulsifiers and preservatives.

The compositions have a very good antibiotic activity on gram $\oplus$ bacteria such as staphylococci, streptococci, pneumococci and are useful in the treatment of infections caused by sensitive germs, particularly, those of staphylococcia such as staphylococcal septicemias, malignant staphylococcia of the face or skin, pyodermatitis, septic or suppurating sores, boils, anthrax, phlegmons, erysipelas and acne, staphylococcia such as acute primary or post-influenzal anginas, bronchopneumonia, pulmonary suppuration, streptococcia such as acute anginas, otitis, sinusitis, scarlet fever, pneumococcia such as pneumonia, bronchitis; brucellosis, diphtheria, gonococcal infection. They are also active against infections caused by gram negative germs such as Haemophilus influenzae, Rickettsies, Mycoplasma pneumoniae, Chlamydia, Legionella, Ureaplasma, Toxoplasma or by germs of the Mycobacterium, Listeria, Meningococcal and Campylobacter type.

The method of the invention for combatting bacterial infections in warm-blooded animals comprises administering to warm-blooded animals an antibacterially effective amount of a compound of formula I or its non-toxic, pharmaceutically acceptable acid addition salts. The compounds may be administered orally, rectally, parenterally or topically on the skin or mucous membranes, preferably orally. The usual daily dose is 0.66 to 4 mg/kg depending on the condition treated, the specific compound and method of administration.

In the following examples, there are described several preferred embodiments to illustrate the invention. However, it is to be understood that the invention is not intended to be limited to the specific embodiments.

EXAMPLE 1: 11, 12-dideoxy-3-de[(2,6-dideoxy-3-C-methyl-3-O-methyl-α-L-ribohexopyranosyl)-oxy]-6-O-methyl-3-oxo-12,11-(oxy-carbonyl-([4-(4-chlorophenyl)-butyl)]-imino))-erythromycin.

STAGE A: 3 -de[(2,6-dideoxy-3-C-methyl-3-O-methyl-α-L-ribohexopyranosyl)-oxy]-6-O-methyl-11-O-(methylsulfonyl)-3 -oxo-erythromycin-2'-acetate.

17 g of 3-de[(2,6-dideoxy-3-C-methyl-3-O-methyl-α-L-ribohexopyranosyl)-oxy]-6-O-methyl-3-oxo-erythromycin-2'-acetate were added with stirring under a nitrogen atmosphere to 100 ml of pyridine and the mixture was cooled to 10° C. 11.9 g of methane sulfonic anhydride were added and the mixture was allowed to return to ambient temperature. The mixture was stirred for 5 hours and the precipitate was filtered, concentrated, taken up with water and extracted with ethyl acetate. The organic phases were washed with water, dried, filtered and concentrated to obtain 20.9 g of the crude desired product which was purified by salification using oxalic acid and then the base was released with ammonium hydroxide to obtain 15.16 g of the desired product melting at 210°–212° C.

STAGE B: 11-deoxy-10,11-didehydro-3-de(2,6-dideoxy-3-C-methyl-3-O-methyl-α-L-ribohexopyranosyl)-oxy)-6-O-methyl-3-oxo-erythromycin-2'-acetate.

8.26 g of the product of Stage A were added with stirring into 35 ml of acetone and then 2.19 ml of DBU were added dropwise. The mixture was stirred at ambient temperature for 20 hours and was then taken up with methylene chloride. The organic phases were washed with water, dried over sodium sulfate, filtered and concentrated to obtain 10 g of product which was taken up in ether followed by separating and washing with ethyl ether to obtain 6.33 g of the desired product melting at 230°–232° C.

STAGE C: 11-deoxy-10,11-didehydro-3-de[(2,6-dideoxy-3-C-methyl-3-O-methyl-α-L-ribohexopyranosyl)-oxy]-12-O-((1 H-imidazole-1-yl)-carbonyl)-6-O-methyl-3-oxo-erythromycin-2'-acetate.

96 mg of sodium hydride as 50% in oil were introduced into 15 ml of tetrahydrofuran and the suspension was cooled to 0° C. A solution of 611 mg of the product of Stage B in 17 ml of tetrahydrofuran was introduced dropwise and a solution of 486 mg of carbonyldiimidazole in 15 ml of tetrahydrofuran was introduced at 0° C. The mixture was stirred for 4 hours 30 minutes and then was allowed to return to ambient temperature, filtered and concentrated. The residue was taken up in ethyl acetate, washed with a solution of sodium dihydrogen phosphate, extracted with ethyl acetate, dried, filtered and concentrated to obtain 852 mg of the desired product which was used as is for the following stage.

STAGE D: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl [(4-(4-chlorophenyl)-butyl]-imino))-erythromycin-2'-acetate.

A solution of 1.1 g of 4-(4-chlorophenyl)-butylamine (prepared as indicated in J. Med. Chem., 1982, Vol. 25, No. 951), 3 ml of acetonitrile and 0.3 ml of demineralized water was added to the 852 mg of product of Stage C. The mixture was stirred for 4 hours at 55° C. and was then poured into a solution of sodium dihydrogen phosphate and extracted with methylene chloride. The extracts were washed with water, dried, filtered and concentrated to obtain 1.4 g of an oil which was chromatographed on silica eluting with a methylene chloride—isopropanol mixture (95-5). The homogeneous fractions were collected using thin layer chromatography, filtered and concentrated to obtain 0.44 g of an oil which was impasted in isopropyl ether, separated and dried at 70° C. to obtain 0.262 g of the desired product melting at 179°–181° C.

STAGE E: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl [(4-(4-chlorophenyl)-butyl]-imino))-erythromycin.

A mixture of 0.23 g of the product of Stage D and 6 ml of methanol was stirred at ambient temperature for 15 hours and the methanol was then evaporated. The residue was chromatographed on silica eluting with an ethyl acetate—methanol—ammonium hydroxide mixture (9-1-0.01). The homogeneous phases were collected using TLC, filtered and concentrated to obtain 0.14 g of an oil which was impasted in isopropyl ether, separated and dried at 80° C. under reduced pressure to obtain 0.094 g of the desired product melting at 194°–196° C. and having a specific rotation of $[\alpha]_D$=+23° (1% in $CHCl_3$).

EXAMPLE 2: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(4-(4-methoxyphenyl)-butyl]-imino])-erythromycin.

STAGE A: 11,12-dideoxy-3-de[(2,6-dideoxy-3 -C-methyl-3-O-methyl-α-L-ribohexopyranosyl)-oxy]-6-O-methyl-3-oxo-12,11-(oxycarbonyl-[(4-(4-methoxyphenyl)-butyl)-imino)]-erythromycin-2'-acetate.

Using the procedure of Example 1, Stage D, 0.8 g of 11-deoxy-10,11-didehydro-3-de[(2,6-dideoxy-3-C-methyl-3-O-methyl-α-L-ribohexopyranosyl)-oxy]-12-O-((1H-imidazole-1-yl)-carbonyl)-6-O-methyl-3-oxo-erythromycin-2'-acetate, 3 ml of acetonitrile and 1.0 g of 4-(4-methoxyphenyl)-butylamine (Tetrahedron Letters, Vol. 32, p. 1699–1702, (1991)), were reacted to obtain 0.8 g of the desired product in the form of a mixture of product which was acetyled and deacetyled in position 2'. Chromatography on silica with methylene chloride-methanol (9-1) was carried out to obtain a product with a Rf=0.47.

STAGE B: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(4-(4-methoxyphenyl)-butyl)-imino)]-erythromycin.

Using the procedure in Example 1, Stage E, 0.8 g of the crude product of Stage A were reacted to obtain 0.237 g of the desired product melting at 193°–195° C. having a specific rotation of $[\alpha]_D$=+22°±3 (C=1% in $CHCl_3$).

EXAMPLE 3: 11,12-dideoxy-3-de[(2,6-dideoxy-3-C-methyl-3-O-methyl -α-L-ribohexopyranosyl)-oxy]-6-O-methyl-3-oxo-12,11-(oxycarbonyl-[(4-(2-thienyl)-butyl)-imino)]-erythromycin-2'-acetate.

STAGE A: 11,12-dideoxy-3-de[(2,6-dideoxy-3-C-methyl-3-O-methyl-α-L-ribohexopyranosy)-oxy]-6-O-methyl-3-oxo-12,11-(oxy carbonyl-[(4-(2-thienyl)-butyl)-imino])-erythromycin-2'-acetate.

Using the procedure of Example 1, Stage D, 0.85 g of 11-deoxy-10,11-didehydro-3-de[(2,6-dideoxy-3-C-methyl-3-O-methyl-α-L-ribohexopyranosyl)-oxy]-12-O-[(1H-imidazol-1-yl )-carbonyl]-6 -O-methyl-3-oxo-erythromycin-2'-acetate, 3 ml of acetonitrile, 0.3 ml of water and 0.822 g of 4-(2-thienyl) butylamine (whose preparation is given hereafter) were reacted to obtain 0.212 g of the desired product melting at 218°–220° C.

STAGE B: 11,12-dideoxy-3-de[(2,6-dideoxy-3-C-methyl-3-O- methyl-α-L-ribohexopyranosyl)-oxy]-6-O-methyl-3-oxo-12,11-(oxycarbonyl-[(4-(2-thienyl)-butyl]-imino))-erythromycin.

Using the procedure in Example 1, Stage E, 0.182 g of the product of Stage A and 6 ml of methanol were reacted to obtain 0.085 g of the desired product melting at 188°–190° C. and having a specific rotation of $[\alpha]_D$+24° (C=1% in $CDCl_3$).

EXAMPLE 4: 11,12 -dideoxy-3-de[(2,6-dideoxy-3-C-methyl-3-O-methyl-α-L-ribohexopyranosyl)-oxy]-6-O-methyl-3-oxo-12,11-(oxycarbonyl-[(4-(1,1'-biphenyl)-4-yl ]-butyl)-imino))-erythromycin.

STAGE A: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(4-(1,1'-biphenyl)-4-yl ]-butyl)-imino))-erythromycin-2'-acetate.

A mixture of 3.5 ml of acetonitrile, 0,7 g of 11-deoxy-10,11-didehydro-3-de[(2,6-dideoxy-3-C-methyl-3-O-methyl-α-L-ribohexopyranosyl)-oxy]-12-O-((1H-imidazol-1-yl)-carbonyl)-6-O-methyl-3-oxo-erythromycin-2'-acetate, 0.3 ml of water, 1.1 g of biphenylbutylamine (preparation given hereafter) was heated at 55° C. for 5 hours and was then poured into a saturated aqueous solution of sodium dihydrogen phosphate, extracted with ethyl acetate and filtered. The aqueous phase was decanted, extracted with ethyl acetate and washed with water followed by drying, filtering and concentrating to obtain 1.1 g of the expected product.

STAGE B: 11,12-dideoxy-3-de[(2,6-dideoxy-3-C-methyl-3-O -methyl-α-L-ribohexopyranosyl)-oxy]-6-O-methyl-3-oxo-12,11-(oxycarbonyl-[(4-(1,1'-biphenyl)-4-yl)-butyl)-imino])-erythromycin.

1.1 g of the product of Stage A was poured into 12 ml of methanol and the solution was stirred for 15 hours at ambient temperature, followed by concentrating, diluting with 3 ml of methylene chloride, drying, filtering and concentrating. The product obtained was crystallized from an isopropyl ether-ethyl ether mixture (9-1) to obtain after separating and drying at 80° C., 0.148 g of product melting at 166°–168° C.

NMR—CDCl$_3$ 1.34(s) and 1.47(s)—6 and 12 CH$_3$; 2.68(m)—CH$_2$—∅; 3.05 to 3.25—H$_{10}$, H$_4$ and H$_2$'; 3.60(s)—H$_{11}$; 3.67(m)

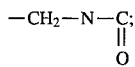

−7.26—7.49—internal phenyl; 7.31 H in para position, −7.42 H in meta position, −7.58 H in ortho position—external phenyl.

| Analysis: | | | |
|---|---|---|---|
| | % Calculated | | % Found |
| C % | 68.75 | C % | 68.6 |
| H % | 8.35 | H % | 8.5 |
| N % | 3.41 | N % | 3.3 |

Using the above procedure, 11-deoxy-10,11-didehydro-3-de[(2,6-dideoxy-3-C-methyl-3-O-methyl-α-L-ribohexopyranosyl)-oxy]-12-O((1H-imidazol-1-yl)-carbonyl)-6-O-methyl-3-oxo-erythromycin-2'-acetate and the appropriate amines were reacted to obtain the following products.

EXAMPLE 5: 11,12-dideoxy-3-de[(2,6-dideoxy-3-C-methyl-3-O-methyl-α-L-ribohexopyranosyl)-oxy]-6-O-methyl-3-oxo-12,11-(oxy-carbonyl-[(4-(2-methoxyphenyl)-butyl)-imino])-erythromycin melting at 190°–192° C. and having a specific rotation of $[\alpha]_D=+24°$ (C=1% in CHCl$_3$).

EXAMPLE 6: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[((2-(phenylmethylthio)-ethyl)-imino])-erythromycin melting at 190°–192° C. and having a specific rotation of $[\alpha]_D=-11.5°$ (C=1% in CHCl$_3$).

EXAMPLE 7: 11,12-dideoxy-3-de[(2,6-dideoxy-3-C-methyl-3-O-methyl-α-L-ribohexopyranosyl)-oxy]-6-O-methyl-3-oxo-12,11-(oxy carbonyl-[(4-(4-nitrophenyl)-butyl)-imino])-erythromycin melting at 200°–202° C. and having a specific rotation of $[\alpha]_D=+15°$ (C=1% in CHCl$_3$).

EXAMPLE 8: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(4-(2,4-dimethylphenyl)-butyl)-imino])-erythromycin melting at 183°–185° C. and having a specific rotation of $[\alpha]_D=+21°$ (C=1% in CHCl$_3$).

EXAMPLE 9: 11,12-dideoxy-3-de[(2,6-dideoxy-3-C-methyl-3-O-methyl-α-L-ribohexopyranosyl)-oxy]-6-O-methyl-3-oxo-12,11-(oxy carbonyl-[(4-(4-methylphenyl)-butyl)-imino])-erythromycin melting at 200°–202° C. and having a specific rotation of $[\alpha]_D=+23°$ (C=1% in CHCl$_3$).

EXAMPLE 10: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(4-(2,4,6-trimethylphenyl)-butyl)-imino])erythromycin melting at 188°–190° C. and having a specific rotation of $[\alpha]_D=+24°$ (C=1% in CHCl$_3$).

EXAMPLE 11: 11,12-dideoxy-3-de[(2,6-dideoxy-3-C-methyl-3-O-methyl-α-L-ribohexopyranosyl)-oxy]-6-O-methyl-3-oxo-12,11-(oxy carbonyl-((4-[(1H)-imidazole-1-yl)-butyl)-imino])-erythromycin melting at 212°–214° C. and having a specific rotation of $[\alpha]_D=+26.2°$ (C=0.85% in CHCl$_3$).

EXAMPLE 12: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(4-(3-methoxyphenyl)-butyl)-imino])-erythromycin melting at 196°–198 ° C. and having a specific rotation of $[\alpha]_D=+18.8$ ° (C=1% in CHCl$_3$).

EXAMPLE 13: 11,12-dideoxy-3-de[(2,6-dideoxy-3-C-methyl-3-O-methyl-α- L-ribohexopyranosyl)-oxy]-6-O-methyl-3-oxo-12,11-(oxy carbonyl-[(4-phenylamino)-4-oxobutyl)-imino])-erythromycin melting at 190°–192° C. and having a specific rotation of $[\alpha]_D=+8°$ (C=1% in CHCl$_3$).

EXAMPLE 14: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(3-(phenylthio)propyl)-imino])-erythromycin melting at 204°–206° C. and having a specific rotation of $[\alpha]_D=+19°$ (C=0.9% in CHCl$_3$).

EXAMPLE 15: 11,12-dideoxy-3-de[(2,6-dideoxy-3-C-methyl-3-O-methyl-α-L-ribohexopyranosyl)-oxy]-6-O-methyl-3-oxo-12,11-(oxy carbonyl-[(2-((phenylcarbonyl)-amino)-ethyl)-imino])-erythromycin melting at 240° C. and having a specific rotation of $[\alpha]_D=-2°$ (C=1% in CHCl$_3$).

EXAMPLE 16: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(3-phenoxypropyl)-imino])-erythromycin melting at 222°–225° C. and having a specific rotation of $[\alpha]_D=+20°$ (C=0.9% in CHCl$_3$).

EXAMPLE 17: 11,12-dideoxy-3-de[(2,6-dideoxy-3-C-methyl-3-O-methyl-α-L-ribohexopyranosyl)-oxy]-6-O-methyl-3-oxo-12,11-([2-(phenylmethoxy)-ethyl)-imino])-erythromycin melting at 207° C.

EXAMPLE 18: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(2-(4-methoxyphenyl)-ethyl)-imino])-erythromycin melting at 218°–220° C. and having a specific rotation of $[\alpha]_D=15.5°$ (C=1% in CHCl$_3$).

EXAMPLE 19: 11,12-dideoxy-3-de[(2,6-dideoxy-3-C-methyl-3-O-methyl-α-L-ribohexopyranosyl)-oxy]-6-O-methyl-3-oxo-12,11-(oxy carbonyl-[(4-(1H-indol-4-yl)-butyl)-imino])-erythromycin melting at 208°–212° C. and having a specific rotation of $[\alpha]_D=+22°$ (C=1% in CHCl$_3$).

EXAMPLE 20: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(4-(3-aminophenyl)-butyl)-imino])-erythromycin melting at 200°–202° C. and 210° C. and having a specific rotation of $[\alpha]_D=+23°$ (C=1% in CHCl$_3$).

EXAMPLE 21: 11,12-dideoxy-3-de[(2,6-dideoxy-3-C-methyl-3-O-methyl-α-L-ribohexopyranosyl)-oxy]-6-O-methyl-3-oxo-12,11-(oxy-carbonyl-[(4-(2-chlorophenyl)-butyl)-imino])-erythromycin melting at 193°–195° C. and having a specific rotation of $[\alpha]=+23°$ (C=1% in CHCl$_3$).

EXAMPLE 22: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(4-(3-chlorophenyl)-butyl)-imino])-erythromycin melting at 191°–193° C. and having a specific rotation of $[\alpha]_D=+22°$ (C=1% in CHCl$_3$).

EXAMPLE 23: 11,12-dideoxy-3-de[(2,6-dideoxy-3-C-methyl-3-O-methyl-α-L-ribohexopyranosyl)-oxy]-6-O-methyl-3-oxo-12,11-(oxy-carbonyl-[(4-(4-hydroxyphenyl)-butyl)-imino])-erythromycin melting at 220°–222° C.

EXAMPLE 24: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(4-(4-(1-oxobutyl)-phenyl)-butyl)-imino])-erythromycin melting at 134°–136° C.

EXAMPLE 25: 11,12-dideoxy-3-de[(2,6-dideox]-[-3-C-methyl-3-O-methyl-α-L-ribohexopyranosyl)-oxy]-6-O-methyl-3-oxo-12,11-(oxy- carbonyl-[(4-(4-(1-oxoethyl)-phenyl)-butyl)-imino])-erythromycin melting at 170°–172° C.

EXAMPLE 26: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(3-(phenylsulfonyl)-propyl)-imino])-erythromycin melting at 202°–204° C. and having a specific rotation of $[\alpha]_D = +21°$ (C=1% in CHCl$_3$).

EXAMPLE 27: 11,12-dideoxy-3-de[(2,6-dideoxy-3-C-methyl-3-O-methyl-α-L-ribohexopyranosyl)-oxy]-6-O-methyl-3-oxo-12,11-(oxy- carbonyl-[(4-(4-butylphenyl)-butyl)-imino])-erythromycin melting at 134°–135° C. and having a specific rotation of $[\alpha]_D = +19.5°$ (C=1% in CHCl$_3$).

EXAMPLE 28: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(4-(4-quinolinyl)-butyl)-imino])-erythromycin melting at 170°–172° C.

EXAMPLE 29: 11,12-dideoxy-3-de[(2,6-dideoxy-3-C-methyl-3-O-methyl-α-L-ribohexopyranosyl)-oxy]-6-O-methyl-3-oxo-12,11-(oxy-carbonyl-[(4-((2,2'-bithiophen)-5-yl)-butyl)-imino])-erythromycin melting at 147°–149° C.

EXAMPLE 30: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(3-oxo-3-((2-thiazolyl)-amino)-propyl)imino-erythromycin.

EXAMPLE 31: 11,12-dideoxy-3-de[(2,6-dideoxy-3-C-methyl-3-O-methyl-α-L-ribohexopyranosyl)-oxy]-6-O-methyl-3-oxo-12,11-(oxy-carbonyl-[(4-(4-ethylphenyl)-butyl)-imino])-erythromycin melting at 191°–193° C. and having a specific rotation of $[\alpha]_{=+20}°$ (C=1% in CHCl$_3$).

EXAMPLE 32: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(4-(4-(4-chlorobenzoyl)-3-methylphenyl)-butyl)-imino])-erythromycin melting at 143°–145° C. and having a specific rotation of $[\alpha]_D = +8°$ (C=1% in CHCl$_3$).

EXAMPLE 33: 11,12-dideoxy-3-de[(2,6-dideoxy-3-C-methyl-3-O-methyl-α-L-ribohexopyranosyl)-oxy]-6-O-methyl-3-oxo-12,11-(oxy-carbonyl-[(4-(9H-fluoren-2-yl)-butyl)-imino])-erythromycin melting at 215°–217° C. and having a specific rotation of $[\alpha]_D = +20°$ (C=1% in CHCl$_3$).

EXAMPLE 34: 11,12-dideoxy-3-de[(2,6-dideoxy-3-C-methyl-3-O-methyl-α-L-ribohexopyranosyl)-oxy]-6-O-methyl-3-oxo-12,11-(oxycarbonyl-[(4-(6-amino-9H-purin-9-yl)-butyl)-imino-erythromycin and having a specific rotation of $[\alpha]_D = +13°$ (C=1% in CHCl$_3$).

EXAMPLE 35: 11,12-dideoxy-3-de[(2,6-dideoxy-3-C-methyl-3-O-methyl-α-L-ribohexopyranosyl)-oxy]-6-O-methyl-3-oxo-12,11-(oxy-carbonyl-[(4-(4-phenoxyphenyl)-butyl)-imino])-erythromycin melting at 154°–156° C. and having a specific rotation of $[\alpha]_D = +16°$ (C=1% in CHCl$_3$).

EXAMPLE 36: 11,12-dideoxy-3-de[(2,6-dideoxy-3-C-methyl-3-O-methyl-α-L-ribohexopyranosyl)-oxy]-6-O-methyl-3-oxo-12,11-(oxy- carbonyl-[(4-(2-phenyl-1H-imidazol-1-yl) -butyl)-imino])-erythromycin melting at 132°–134° C. and having a specific rotation of $[\alpha]_D = +13°$ (C=1% in CHCl$_3$).

EXAMPLE 37: 11,12-dideoxy-3-de[(2,6-dideoxy-3-C-methyl-3-O-methyl-α-L-ribohexopyranosyl)-oxy]-6-O-methyl-3-oxo-12,11-(oxy-carbonyl-[4-(4-fluorophenyl)-butyl)-imino])-erythromycin melting at 180° C.

EXAMPLE 38: 11,12-dideoxy-3-de[(2,6-dideoxy-3-C-methyl-3-O-methyl-α-L-ribohexopyranosyl)-oxy]-6-O-methyl-3-oxo-12,11-(oxy- carbonyl-[(4-1H-benzimidazol-1-yl)-butyl]-imino])-erythromycin melting at 194°–196° C. and having a TLC: Rf=0,43 (CH$_2$Cl$_2$—MeOH—NH$_4$OH 95-5-0,2).

EXAMPLE 39: 11,12-dideoxy-3-de[(2,6-dideoxy-3-C-methyl-3-O-methyl-α-L-ribohexopyranosyl)-oxy]-6-O-methyl-3-oxo-12,11-(oxy- carbonyl-[(4-(2-phenyl-5-thiazolyl)-butyl]-imino])-erythromycin melting at 118°–120° C. and having a TLC: Rf=0,24 (ACOEt containing 4% T.E.A.

Using the above procedure, the compounds of the following formula I were prepared:

| Z | R |
|---|---|
| H | 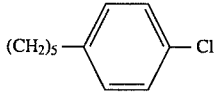 |
| H | 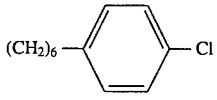 |
| H | 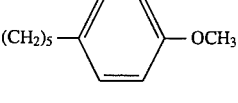 |
| H | 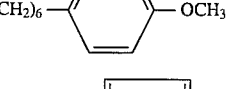 |
| H | 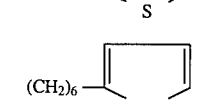 |
| H<br>H | 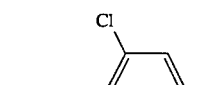 |
| H | 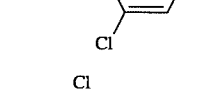 |
| H | 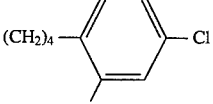 |
| H | 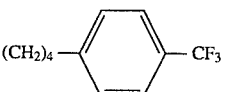 |
| H | 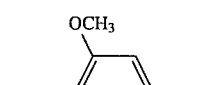 |

| Z | R |
|---|---|
| H | -(CH$_2$)$_4$-(2,6-dimethoxyphenyl) |
| H | -(CH$_2$)$_4$-(3,5-dimethoxy-4-methylphenyl) |
| H | -(CH$_2$)$_4$-(4'-ethyl-biphenyl-4-yl) |
| H | -(CH$_2$)$_4$-(4-aminophenyl) |
| H | -(CH$_2$)$_4$-(4-trifluoromethylphenyl) |
| H | -(CH$_2$)$_4$-(5-methylthiophen-2-yl) |
| H | -(CH$_2$)$_4$-(3-nitrophenyl) |
| H | -(CH$_2$)$_4$-(4'-chloro-biphenyl-4-yl) |
| H | -(CH$_2$)$_5$-(4'-methoxy-biphenyl-4-yl) |
| H | -(CH$_2$)$_6$-(biphenyl-4-yl) |
| H | -(CH$_2$)$_6$-(4'-chloro-biphenyl-4-yl) |
| H | -(CH$_2$)$_5$-(3-chlorophenyl) |
| H | -(CH$_2$)$_5$-(3-nitrophenyl) |
| H | -(CH$_2$)$_6$-(3-chlorophenyl) |
| H | -(CH$_2$)$_6$-(3-nitrophenyl) |
| H | -(CH$_2$)$_5$-(3-methoxyphenyl) |
| H | -(CH$_2$)$_6$-(4'-methoxy-biphenyl-4-yl) |
| H | -(CH$_2$)$_4$-(biphenyl-3-yl) |
| H | -(CH$_2$)$_4$-(4-phenoxyphenyl) |
| H | -(CH$_2$)$_4$-(thiazol-2-yl) |

PREPARATION 1: 4-(2-thienyl)-butylamine

STAGE A: 4-(2-thienyl)-butylamide

A mixture of 40 ml of dichloroethane, 5.1 ml of 4-(2-thienyl)-butyric acid and 10.2 ml of thionyl chloride was stirred for 3 hours at 60° C. and the dichloroethane was evaporated. The product was poured into concentrated ammonium hydroxide and cooled to 0° C. Separation was carried out and the product was dried to obtain 4.29 g of product which was chromatographed on silica eluting with a methylene chloride-methanol mixture (92-8). The homogeneous fractions were collected using TLC, concentrated and filtered. The product was impasted in isopropyl ether, separated and dried to obtain 1.18 g of the desired product melting at 84°–86° C.

STAGE B: 4-(2-thienyl)-butylamide 1.1 g of 4-(2-thienyl)-butylamine were introduced dropwise at 0° C. into a mixture of 30 ml of tetrahydrofuran and 1.06 g of lithium aluminium hydride and the mixture was allowed to return to ambient temperature. After stirring at ambient temperature for 4 hours 30 minutes, then for 1 hour at 30° C. and for 16 hours at ambient temperature and after cooling down to 0° C., 3 ml of a water—tetrahydrofuran mixture (2-1) were added. Then, 8 ml of water were added and then 6 ml of a saturated solution of sodium and potassium tartrate double salt were added. After filtering and concentrating, the product was taken up in ether, washed with sodium carbonate, then with water and the aqueous phases were extracted with ethyl ether. The combined organic phases were dried over sodium sulfate, extracted with ethyl ether. The combined organic phases were dried over sodium sulfate, filtered and concentrated to obtain 0.91 g of a product which was dissolved in 12 ml of an ethyl acetate ethanol mixture (95-5). After cooling to 0° C., a solution of gaseous hydrochloric acid in ethyl acetate was added and the hydrochloride of the expected product precipitated. After separating and drying, 0.675 g of the desired product were obtained in the form of the hydrochloride melting at 168°–170° C. The corresponding base was obtained by alkaline treatment, extraction with ethyl acetate, drying over sodium sulfate, filtration and concentration.

PREPARATION 2: 4-[(1,1'-biphenyl)-4-yl]-butylamine

STAGE A: N-[4-[(1,1'-biphenyl)-4-yl]-3-butenyl-phthalimide

A suspension of 150 ml of tetrahydrofuran, 5.46 g of 4-phenyl-benzaldehyde and 15.9 g of N-(3-bromopropyl) phthalimide triphenyl phosphonium bromide was cooled to −40° C. and then, 3.37 g of potassium terbutylate were introduced. The temperature was allowed to rise to −15° C. and the mixture was stirred at −15° C. for 1 hour and was poured onto ice. The mixture was extracted with ethyl acetate, washed with water and the organic phases were dried over $Na_2SO_4$, filtered and concentrated to obtain 19 g of product. The latter was dissolved in methylene chloride and chromatographed on silica eluting with an ethyl acetate—hexane mixture (3-7). After concentrating, impasting in hexane, separating and drying under reduced pressure, 8.5 g of desired product melting at 112°–114° C. were isolated.

Analysis:

| | % Calculated | | % Found |
|---|---|---|---|
| C % | 81.56 | C % | 81.4 |
| H % | 5.42 | H % | 5.3 |
| N % | 3.96 | N % | 3.8 |

STAGE B: 4-[(1,1'-biphenyl)-4-yl]-3-butenylamine

A mixture of 280 ml of ethanol, 7.9 g of the product of Stage A and 1.3 ml of hydrazine hydrate was refluxed and the reaction was allowed to return to ambient temperature. The precipitate was filtered and washed with ethanol, followed by concentrating, pouring into a 2N hydrochloric acid solution and extracting with ethyl acetate. The organic phases were washed with water, dried, filtered and concentrated under reduced pressure to obtain 2.89 g of the desired product melting at 188°–194° C.

STAGE C: 4-[(1,1'-biphenyl)-4-yl]-butylamine 17 ml of methanol, 1.74 g of the product of Stage B and 0.17 g of 10% Pd on charcoal catalyst were placed in a hydrogenation apparatus and hydrogenation was maintained overnight. After filtering, washing and concentrating, the product was impasted in ethyl acetate, chilled, separated and dried under reduced pressure at 80° C. to obtain 1.55 g of the desired product melting at 260° C.

PREPARATION 3: 4-(2,4,6-trimethylphenyl)-butylamine

Using the procedure of Preparation 2, the desired product was obtained in the form of the hydrochloride melting at 218°–220° C.

PREPARATION 4: 4-(4-methylphenyl)-butylamine

Using the procedure of Preparation 2, the desired product melting at 202°–204° C. was obtained.

PREPARATION 5: 4-(2,4-dimethylphenyl)-butylamine

Using the procedure of Preparation 2, the desired product melting at 126°–128° C. was obtained.

PREPARATION 6: 4-(2-methoxyphenyl)-butylamine

Using the procedure of Preparation 2, the desired product melting at 122°–124° C. was obtained.

PREPARATION 7: 4-(4-phenoxyphenyl)-butylamine

Using the procedure of Preparation 2, the desired product melting at 172°–174° C. was obtained in the form of the hydrochloride which product was converted into the amine by extraction with ethyl acetate in an ammonium hydroxide medium.

PREPARATION 8: 4-(2-phenyl-1H-imidazol-1-yl)-butylamine

STAGE A: N-[4-(2-phenyl-1H-imidazol-1-yl)-butyl-phthalimide 4.32 g of 2-phenyl-imidazole in solution in 25 ml of dimethyl-formamide were added over 75 minutes at ambient temperature to 1.73 g of sodium hydride in 5 ml of dimethylformamide and then, 10.97 g of N-(4-bromobutyl)-phthalimide in 33 ml of dimethylformamide were added. The mixture was stirred for 48 hours at ambient temperature and extraction was carried out with ethyl acetate, followed by drying. The solvent has evaporated and the residue was chromatographed on silica (eluant: ethyl acetate-methylethylamine 95-5). The residue was taken up in ether, chilled and the crystals were separated out and dried to obtain 1.11 g of the expected product melting at 82°–84° C.

STAGE B: 4-(2-phenyl-1H-imidazol-1-yl)-butylamine 1.6 ml of hydrazine hydrate were added to 5.64 g of the product of Stage A in solution in 175 ml of ethanol and the reaction mixture was refluxed for 16 hours. The solvent was eliminated and the residue was taken up in 25 ml of 2N sodium hydroxide and 50 ml of water. Extraction was carried out with ethyl acetate and the extracts were dried. The solvent was evaporated and the residue was chromatographed on silica (eluant: methylene chloride-methanol-ammonium hydroxide 9-1-0.02) to obtain 1.95 g of the expected product with a Rf=0.12.

PREPARATION 9: 4-(6-amino-9H-purin-9-yl)-butylamine

STAGE A: N-[4-(6-amino-9H-purin-9-yl)-3-butenyl]-phthalimide 3.4 g of sodium hydride were added to 9.6 g of adenine in 270 ml of dimethylformamide and the mixture was stirred for 2 hours and 30 minutes. 20 g of N-(4-bromobutyl)-phthalimide were added and the mixture was stirred at ambient temperature for 74 hours, followed by filtering. The solvent of the filtrate was evaporated and the precipitate was washed with ether, with water, with ethanol, then again with ether and dried. The residue was dissolved in methanol at 65° C. and chilled to obtain 15.00 g of the expected product.

STAGE B: 4-(6-amino-9H-purin-9-yl)-butylamine 14.01 g of the product of Stage A in 728 ml of ethanol and 2.02 ml of hydrazine was refluxed for 22 hours. Another 2.02 ml of hydrazine were added and the reaction was continued for 11 hours. The reaction medium was allowed to return to ambient temperature, then filtered. The ethanol was evaporated off and dried to obtain 10.5 g of crude product.

8.72 g of the crude product was taken up in 50 ml of methylene chloride and 9.42 ml of trifluroracetic acid were added. The reaction medium stood for 16 hours at ambient temperature and the precipitate was taken up in ether, filtered and dried to obtain 10.24 g of the expected product in the form of trifluoroacetate.

PREPARATION 10: 4-(1H-benzimidazol-1-yl)-butylamine

Using the procedure of Preparation 8, 4,13 g of benzimidazole were reacted to obtain 7,97 g of the intermediate phthalimide (melting at 136°–138° C.) were obtained which was reacted with 2,5 ml of hydrazine hydrate to obtain 4,99 g of the expected product, the oxalate of which was obtained after treatment with oxalic acid.

PREPARATION 11: 2-phenyl-5-(4-aminobutyl)-thiazole

Using the procedure of Preparation 2, the expected product was obtained melting at 62°–64° C.

EXAMPLES OF PHARMACEUTICAL COMPOSITIONS

Tablets were prepared containing 150 mg of the product of Example 1, 2, 3, 4 or 5 and sufficient excipient (starch, talc, magnesium stearate for a 1 g tablet.

| Product of Example 1 | 150 mg |
| --- | --- |

PHARMACOLOGICAL STUDY OF THE PRODUCTS OF THE INVENTION Method of dilutions in liquid medium A series of tubes was prepared into which an equal quantity of sterile nutritive medium was divided and increasing quantities of the product to be studied were distributed into each tube. Then, each tube was seeded with a bacterial strain and after incubation for 24 hours in a heating chamber at 37° C., the growth inhibition was evaluated by transillumination which allowed the minimal inhibiting concentrations (M.I.C.), expressed in micrograms/ml to be determined. The following results were obtained:

| Products | GRAM+ BACTERIAL STRAINS | | | | | |
| --- | --- | --- | --- | --- | --- | --- |
|  | Ex. 1 | Ex. 2 | Ex. 3 | Ex. 4 | Ex. 11 | Ex. 15 |
| Staphylococcus aureus 011UC4 | 0.08 | 0.08 | 0.04 | 0.15 | 0.08 | 0.04 |
| Staphylococcus aureus 011HT17 | 0.08 | 0.08 | 0.04 | — | — | — |
| Staphylococcus aureus 011G0251 | 0.08 | 0.15 | 0.08 |  | 0.15 |  |
| Staphylococcus epidermidis 012GO11I | 0.08 | 0.08 | 0.08 | 0.6 | 0.6 | 0.08 |
| Streptococcus pyogenes group A 02A1UC1 | ≦0.02 | ≦0.02 | ≦0.02 | 0.04 | ≦0.02 | 0.04 |
| Streptococcus agalactiae group B 02B1HT1 | 0.15 | 0.15 | 0.08 | ≦0.02 | ≦0.02 | ≦0.02 |

| Products | GRAM+ BACTERIAL STRAINS | | | | | |
| --- | --- | --- | --- | --- | --- | --- |
|  | Ex. 1 | Ex. 2 | Ex. 3 | Ex. 4 | Ex. 11 | Ex. 15 |
| Streptococcus sp group C 02C0CB3 | ≦0.02 | ≦0.02 | ≦0.02 |  |  |  |
| Streptococcus faecalis group D 02D2UC1 | 0.08 | ≦0.02 | ≦0.02 | 0.04 | ≦0.02 |  |
| Streptococcus faecium group D 02D3HT1 | 0.08 | 0.04 | ≦0.02 | 0.04 | ≦0.02 | 0.04 |
| Streptococcus sp group G 02G0GR5 | 0.04 | ≦0.02 | ≦0.02 | 0.04 | ≦0.02 | ≦0.02 |
| Streptococcus mitis 02mitGR16I | ≦0.02 | ≦0.02 | ≦0.02 | 0.15 | 0.15 |  |
| Streptococcus agalactiae group B 02B1SJ1 |  |  |  | 0.6 | 0.3 |  |
| Streptococcus sp group C 02C0CB1 | 0.3 | 0.3 | 0.6 | 0.6 | 0.3 | 0.15 |
| Streptococcus sp group C 02COCB1 | 0.15 | 0.15 | 0.3 | — |  |  |
| Streptococcus pneumoniae 032UC1 | 0.08 | 0.08 | 0.04 | ≦0.02 | ≦0.02 | ≦0.02 |
| Streptococcus pneumoniae 030SJ5 | 0.08 | 0.15 | 0.15 | 0.15 | 0.3 | 0.15 |

Furthermore, the products of Examples 1, 2, 3, 4, 11 and 15 displayed a useful activity on the following GRAM⊖ bacterial strains: Hamemophilus Influenzae 351HT3, 351CB12, 351CA1 and 351GR6.

Various modifications of the products and methods of the invention may be made without departing from the spirit or scope of thereof and it is to be understood that the invention is intended to be limited only as defined in the appended claims.

What is claimed is:

1. A compound having a formula selected from the group consisting of

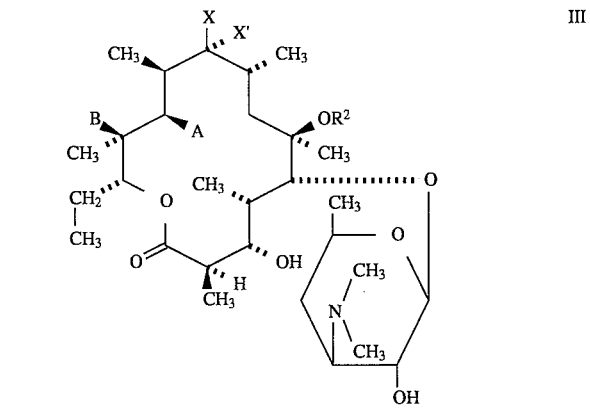

III

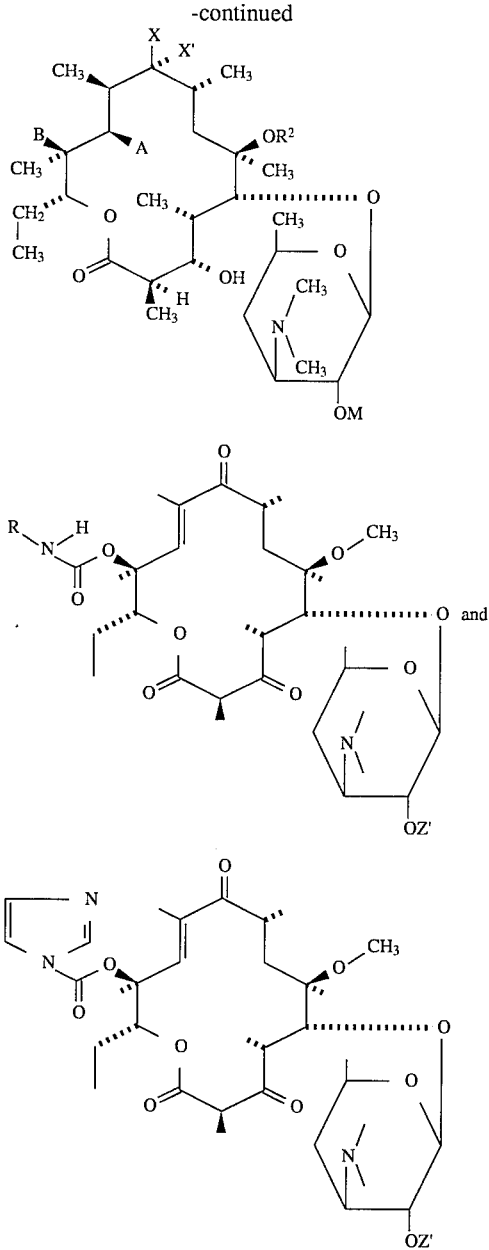

wherein R', is an easily cleavable ester of an acid selected from the group consisting of sulfonic acid, methane sulfonic acid, p-toluene sulfonic acid and trifluoromethane sulfonic acid, Z' is an acyl of an organic carboxylic acid of up to 18 carbon atoms and R is $-(CH_2)_n-Ar_1$ or $-XAr_2$, n is an integer from 1 to 7, $Ar_1$ and $Ar_2$ are individually selected from the group consisting of a) carbocyclic aryl of up to 18 carbon atoms substituted by at least one member of the group consisting of free carboxy, alkoxycarbonyl and carboxyl salified with a pharmaceutically acceptable base, —OH, halogen,

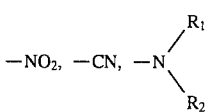

,alkyl, cycloalkyl, alkenyl, alkynyl, alkoxy, alkylthio, alkenyloxy, alkynyloxy, alkenylthio, alkynylthio, N-alkyl, N-alkenyl and N-alkynyl of up to 12 carbon atoms optionally substituted with at least one halogen, $R_1$ and $R_2$ are individually hydrogen or alkyl of 1 to 12 carbon atoms, b)

wherein $R_3$ is selected from the group consisting of alkyl of 1 to 12 carbon atoms, optionally substituted carbocyclic aryl, carbocyclic aryloxy and carbocyclic arylthio, optionally substituted heterocyclic selected from the group consisting of thienyl, furyl, pyrrolyl, thiazolyl, oxazolyl, imidazolyl, thiadiazolyl, pyrazolyl, pyridyl, pyrimidinyl, pyridazinyl, indolyl, benzofuryl, benzothienyl, quinolinyl and a purine base remainder with the optional substituents being those of carbocyclic aryl above and X is an alkyl of 1 to 6 carbon atoms interrupted by a member of the group consisting of —O—, —S—, —SO—, $SO_2$, —CO—,

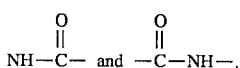

2. A compound of claim 1 selected from the group consisting of 11-deoxy-10,11-didehydro-3-de[(2,6-dideoxy-3-C-methyl-3-O-methyl-α-L-ribohexopyranosyl)-oxy]-6-O-methyl-3-oxo-erythromycin-2'-acetate and its corresponding 2'hydroxy compound, 4-(2-thienyl)-butylamine, 4-(1,1'-biphenyl)-butylamine, 4-(4-methylphenyl)-butylamine, 4-(2,4-dimethyl-phenyl)-butylamine, 4-(2,4,6-trimethylphenyl)-butylamine and 4-(2-methoxyphenyl)-butylamine.

* * * * *